(12) United States Patent
Ottens et al.

(10) Patent No.: US 6,567,166 B2
(45) Date of Patent: May 20, 2003

(54) FOCUSED LASER LIGHT TURBIDITY SENSOR

(75) Inventors: Gregory J. Ottens, Freeport, IL (US); Kevin J. Engler, Freeport, IL (US); Thomas R. Guiffre, Freeport, IL (US); Thomas M. Moyer, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/788,723

(22) Filed: Feb. 20, 2001

(65) Prior Publication Data

US 2002/0159061 A1 Oct. 31, 2002

(51) Int. Cl.[7] .................. G01N 15/06; G01N 21/00
(52) U.S. Cl. ........................ 356/343; 356/339
(58) Field of Search ................. 356/343, 339, 356/442, 441, 340, 440, 432, 436, 341, 338, 337; 250/574

(56) References Cited

U.S. PATENT DOCUMENTS

| | | | |
|---|---|---|---|
| 3,713,743 A | 1/1973 | Simms | 356/338 |
| 3,880,526 A | 4/1975 | Kobayashi et al. | 356/442 |
| 4,152,070 A | 5/1979 | Kushner et al. | 356/343 |
| 4,193,692 A | 3/1980 | Wynn | 356/341 |
| 4,198,161 A | 4/1980 | Larson | 356/339 |
| 4,263,511 A | 4/1981 | Hirschberg | 250/343 |
| 4,497,577 A | 2/1985 | Sato et al. | 356/336 |
| 4,999,514 A | 3/1991 | Silveston | 250/575 |
| 5,012,119 A | 4/1991 | Rhiner | 250/574 |
| 5,025,169 A | 6/1991 | Arakawa et al. | 250/574 |
| 5,140,168 A * | 8/1992 | King | 250/575 |
| 5,291,626 A | 3/1994 | Molnar et al. | 8/158 |
| 5,331,177 A | 7/1994 | Kubisiak et al. | 250/574 |
| 5,408,307 A | 4/1995 | Yamamoto et al. | 356/73 |
| 5,444,531 A | 8/1995 | Foreman et al. | 356/341 |
| 5,446,531 A | 8/1995 | Boyer et al. | 356/72 |
| 5,485,013 A * | 1/1996 | Cummins | 250/574 |
| 5,489,977 A | 2/1996 | Winslow | 356/73 |
| 5,565,984 A | 10/1996 | Girvin | 356/336 |
| 5,589,935 A * | 12/1996 | Biard | 356/339 |
| 5,596,408 A | 1/1997 | Cummins et al. | 356/339 |
| 5,603,233 A | 2/1997 | Erickson et al. | 68/12.02 |
| 5,604,590 A | 2/1997 | Cooper et al. | 355/70 |
| RE35,566 E | 7/1997 | Boyer et al. | |
| 5,729,025 A | 3/1998 | Erickson et al. | 250/574 |
| 5,740,733 A * | 4/1998 | Mungenast | 101/116 |

(List continued on next page.)

FOREIGN PATENT DOCUMENTS

| | | |
|---|---|---|
| DE | 296 22 293 U | 3/1997 |
| DE | 198 06 559 A | 8/1999 |
| WO | WO 99 36772 A | 7/1999 |

OTHER PUBLICATIONS

PCT International Search Report, dated Mar. 4, 2002, relevant to PCT counterpart of related U.S. patent application.

*Primary Examiner*—Georgia Epps
*Assistant Examiner*—Omar Hindi
(74) *Attorney, Agent, or Firm*—Kris T. Frederick

(57) ABSTRACT

A turbidity sensor for measuring a full range of particulate content in a turbid environment, including a method thereof. The turbidity sensor includes a laser light source for emitting laser light through the particulate content. The turbidity sensor additionally includes at least one light-sensitive detector located proximate to the laser light source for the detection of light scattered from particles of the particulate content that come into contact with laser light emitted from the laser light source, thereby permitting the accurate measurement of the turbidity of the turbid environment. A plurality of light-sensitive detectors may be employed, including a back scatter detector, a side scatter detector, a forward scatter detector, and a direct transmission detector. The light-sensitive detectors may be arranged in a geometric configuration of light-sensitive detectors with respect to the laser light source.

50 Claims, 6 Drawing Sheets

U.S. PATENT DOCUMENTS

| | | | |
|---|---|---|---|
| 5,757,481 A | 5/1998 | O'Brien et al. | 356/239.1 |
| 5,793,485 A | 8/1998 | Gourley | 356/318 |
| 5,800,628 A | 9/1998 | Erickson et al. | 134/18 |
| 5,828,458 A * | 10/1998 | Taylor et al. | 356/440 |
| 5,872,361 A | 2/1999 | Paoli et al. | 250/341.8 |
| 5,881,578 A | 3/1999 | Proppe et al. | 68/12.02 |
| 5,889,192 A | 3/1999 | Engel | 73/1.02 |
| 5,906,802 A | 5/1999 | Langford | 422/300 |
| 5,923,433 A | 7/1999 | Giuffre et al. | 356/440 |
| 5,957,144 A | 9/1999 | Neff et al. | 134/56 |
| 6,007,640 A | 12/1999 | Neff et al. | 134/18 |
| 6,052,184 A | 4/2000 | Reed | 356/338 |
| 6,062,476 A * | 5/2000 | Stern et al. | 235/462.35 |
| 6,141,097 A | 10/2000 | Herman | 356/335 |
| 6,456,375 B1 * | 9/2002 | Ottens et al. | 356/339 |
| 2002/0159061 A1 * | 10/2002 | Ottens et al. | 356/338 |

* cited by examiner

FOCUSED LASER LIGHT TURBIDITY SENSOR

RELATED APPLICATIONS

This application is related to co-pending and co-owned patent applications entitled: "Focused Laser Light Turbidity Sensor Apparatus and Method for Measuring Very Low Concentrations of Particles in Fluids," U.S. Ser. No. 09/788,724, filed on Feb. 20, 2001 now U.S. Pat. No. 6,456,375.

TECHNICAL FIELD

The present invention relates to sensor methods and systems. The present invention also relates to sensors that measure the turbidity and quality of having particulate content. The present invention also relates to semiconductor-based sensors. The present invention additionally relates to photodiode-based sensor devices and methods thereof. The present invention also relates to laser emitting sensor devices and methods thereof. Finally, the present invention relates to turbidity sensors that monitor the status of a fluid and determine the presence or level of impurities in the fluid.

BACKGROUND OF THE INVENTION

Reducing the amount of energy consumed by a machine for cleansing articles, such as a clothes washer, is a significant problem. In such a machine, the amount of energy consumed is primarily determined by the amount of energy needed to heat the liquid, such as water, used to cleanse the articles. Thus, decreased liquid consumption for such machines may result in a significant improvement in energy efficiency.

Appliances for cleansing articles, such as clothes washers, are typically preprogrammed to perform a complete washing in a predetermined number of wash cycles, each wash cycle having a predetermined duration. A wash cycle may provide substantially particle-free liquid to the machine, circulating the liquid during the wash cycle, and draining or flushing the liquid from the machine after its having been used to wash or cleanse the articles. Often the machine user may select from a limited number of preprogrammed options. Such preprogramming does not use energy efficiently because the machine may either perform an excessive number of wash cycles, or perform each cycle for an excessive duration, to assure that cleanliness of the articles is achieved. To improve the energy efficiency of such appliances, closed loop feedback control systems can be incorporated into the washing machine. Several techniques have been utilized to indirectly monitor cleanliness of the articles during closed loop feedback control of the appliance, including use of a device for measuring the turbidity of the liquid used to wash the articles.

Devices for measuring turbidity that detect the transmission of light propagated through water used to wash the articles have been employed to ascertain information about progress of the wash; however, such devices have not been ideal for use in household appliances. Such devices are oftentimes difficult or non-economic to implement due to the electronic circuitry necessary to perform the complex turbidity measurements. Furthermore, such devices are subject to measurement error. Factors such as water turbulence, cloudiness of the water sample chamber, light source dimming, or device performance degradation may cause attenuation of the amount of light detected and thus affect measurement accuracy. The precision of such devices is also not entirely satisfactory. This imprecision has the additional effect of making turbidity measurements provided by such devices difficult to interpret in a closed loop feedback control system.

Manufacturers of washing machines thus desire to control the washing algorithms with such machines in order to maintain high washability standards and increase energy efficiency. Turbidity measurement must be accurate over a broad range of washing cycles and turbid environments in order to make proper decisions during washing cycles.

Turbidity sensors can be utilized to monitor turbidity in liquids operating within turbid environments, such as a washing machine. Turbidity sensors monitor the status of a fluid and more particularly determine the presence or level of impurities in the fluid. Often the presence of impurities determines the suitability of the fluid for use in its intended purpose. As an example, lubricating oil having too high a contamination level should be cleansed or changed.

Turbidity sensors are thus utilized in many different types of applications, for example, in association with machines for washing articles, such as dishwashers and washing machines. Most turbidity sensors measure the effect on a light beam of particulate matter suspended within a fluid. Some turbidity sensors utilize only a transmitted light signal, while others utilize both scattered and transmitted light.

Certain prior art turbidity sensors operate by shining a light into a test cell that contains the fluid under scrutiny. The degree to which the light is transmitted as well as scattered gives an indication of the turbidity or pureness of the fluid sample. The previously known turbidity sensors often use light emitting diodes (LEDs) for light sources and the use of photodiodes and phototransistors for use as detectors to reduce costs. An output from such systems may employ light intensity to frequency converters. For example, a photodiode or phototransistor that monitors light intensity is coupled to such a converter to generate a signal whose frequency corresponds to and varies with the turbidity level of the fluid.

A problem identified in prior art turbidity sensors is that the light source that shines light into the fluid sample can change its emission characteristics with time or with variations in temperature. Similarly, changes in operating characteristics can take place in the sensors that are used to sense the light that travels through the fluid.

Prior art turbidity sensors have experienced problems when trying to sense the condition of fluids that are either at low or high turbidity levels. In addition, the sensor's test cell must be large enough to pass all suspended particles in the test material without fouling. The test cell must also be small enough, however, to allow light to be transmitted through the cell and received by a sensor on the opposite side of the test cell from the source. At high turbidity levels, a long transmission path will not pass enough light to allow the sensor to provide a meaningful measurement as the variation in light output, such as a frequency. Conversely, at low turbidity levels, a test cell's transmission path may be too short to allow sufficient light to be scattered or absorbed to produce a meaningful measurement. The use of such test cells or sample cells is thus inefficient and difficult to implement.

Many fluid filters for liquids and gases function by particle entrapment. As filters gradually become clogged by the particles, detection of the need for cleaning or replacement is often accomplished by mass air flow measurements downstream of the filter, pressure drop measurements across the filter and motor or pump loading. All of these techniques have disadvantages in terms of cost, accuracy or reliability.

In addition, the structure and assembly of previously known turbidity sensors is often complex, particularly where the structure supports for the components are arranged to avoid improper alignments of the components with respect to each other. As a result, any supports for the component that are adjustable so as to permit a final alignment of the parts after assembly are quite complex and costly. Moreover, the previously known components and the support structures for the components are not well adapted for simple and economical mass production, and the assembly of products employing turbidity sensors that otherwise would be readily mass produced can be substantially complicated by installation of the previously known support structures and component assemblies. In addition, the performance of systems using light sensors can be substantially affected by temperature changes and component changes due to aging, contamination and the like.

The incorporation of turbidity sensors into a machine for washing articles, such as a washing machine or dishwasher, can increase the cost of the machine by a significant amount because of the complexity of such known turbidity sensors. Typically, a turbidity sensor can include a microprocessor, which controls the operation of the turbidity sensor and analyzes the signals received thereby to determine the magnitude of turbidity of the water within the machine for washing articles. It would be beneficial if the operation of a turbidity sensor could be significantly simplified and, as a result, the costs of the turbidity sensor significantly reduced.

One beneficial use to which a turbidity sensor can be applied is the conservation of water during the operation of a machine for washing articles. The repeated draining and refilling of a machine for washing articles uses a significant amount of water and, if it is not excessively dirty, the draining of the water can represent a significant waste of water. The appropriate use of a turbidity sensor can avoid the unnecessary draining and refilling of machines for washing articles.

A need thus exists for a device, including systems and methods thereof, for measuring turbidity in a simple and economic manner and which overcomes the aforementioned problems associated with prior art turbidity sensors. A low-cost sensing of turbidity is needed in a machine for washing articles where a full range of particulate content must be measured. In addition, accurate measurement of turbidity is needed in other applications, such as water quality systems, hydraulic oils, or any other application where fluid quality is measured.

BRIEF SUMMARY OF THE INVENTION

The following summary of the invention is provided to facilitate an understanding of some of the innovative features unique to the present invention, and is not intended to be a full description. A full appreciation of the various aspects of the invention can be gained by taking the entire specification, claims, drawings, and abstract as a whole.

It is one aspect of the present invention to provide sensor methods and systems.

It is another aspect of the present invention to provide a sensor that measures the turbidity and quality of fluids and viscous environments having particulate content.

It is also an aspect of the present invention to provide a semiconductor-based sensor.

It is an additional aspect of the present invention to provide photodiode-based sensor methods and systems.

It is another aspect of the present invention to provide laser emitting sensor devices and methods thereof.

It is still another aspect of the present invention to provide turbidity sensors that monitor the status of a fluid or viscous environment and determine the presence or level of impurities in the fluid or viscous environment.

The above and other aspects are achieved as is now described in a turbidity sensor for measuring a full range of particulate content in a turbid environment, including a method thereof. The turbidity sensor includes a light source, such as a laser light source, for emitting light through the particulate content. The type of light emitted through the particulate content is preferably laser light. The turbidity sensor additionally includes at least one light-sensitive detector located proximate to the laser light source. Such a light-sensitive detector is utilized for the detection of light scattered from particles of the particulate content that come into contact with laser light emitted from the laser light source, thereby permitting the accurate measurement of the turbidity of the turbid environment. A plurality of light-sensitive detectors may be employed, including a back scatter detector, a side scatter detector, a forward scatter detector, and a direct transmission detector. The light-sensitive detectors may be arranged in a geometric configuration of light-sensitive detectors with respect to the laser light source. The laser light source may be a VCSEL or other laser light source.

The turbidity sensor and method thereof are based on the utilization of a low-cost diode with a focusing lens to create a focused and strong beam of light, capable of passing through a wide range of fluids. This light source is unique in turbidity applications because of its focused beam and intense power that can pass through a wide range of turbidity levels in many different solutions. Because the beam of light emitted from this laser light source is focused, light detectors can be placed closer to the incident beam.

Additionally, the use of a low-cost semiconductor laser diode provides a highly accurate and powerful light source to create a low-cost turbidity sensor. This light source, coupled with various geometric configurations of light-sensitive detectors can accurately measure a broad range of particulate concentrations. Such semiconductor light detectors may be configured in several geometric locations with respect to the light source, including direct transmitted, side scatter, forward, scatter, or back scatter.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate an embodiment of the present invention and are not intended to limit the scope of the invention.

Figure 1:
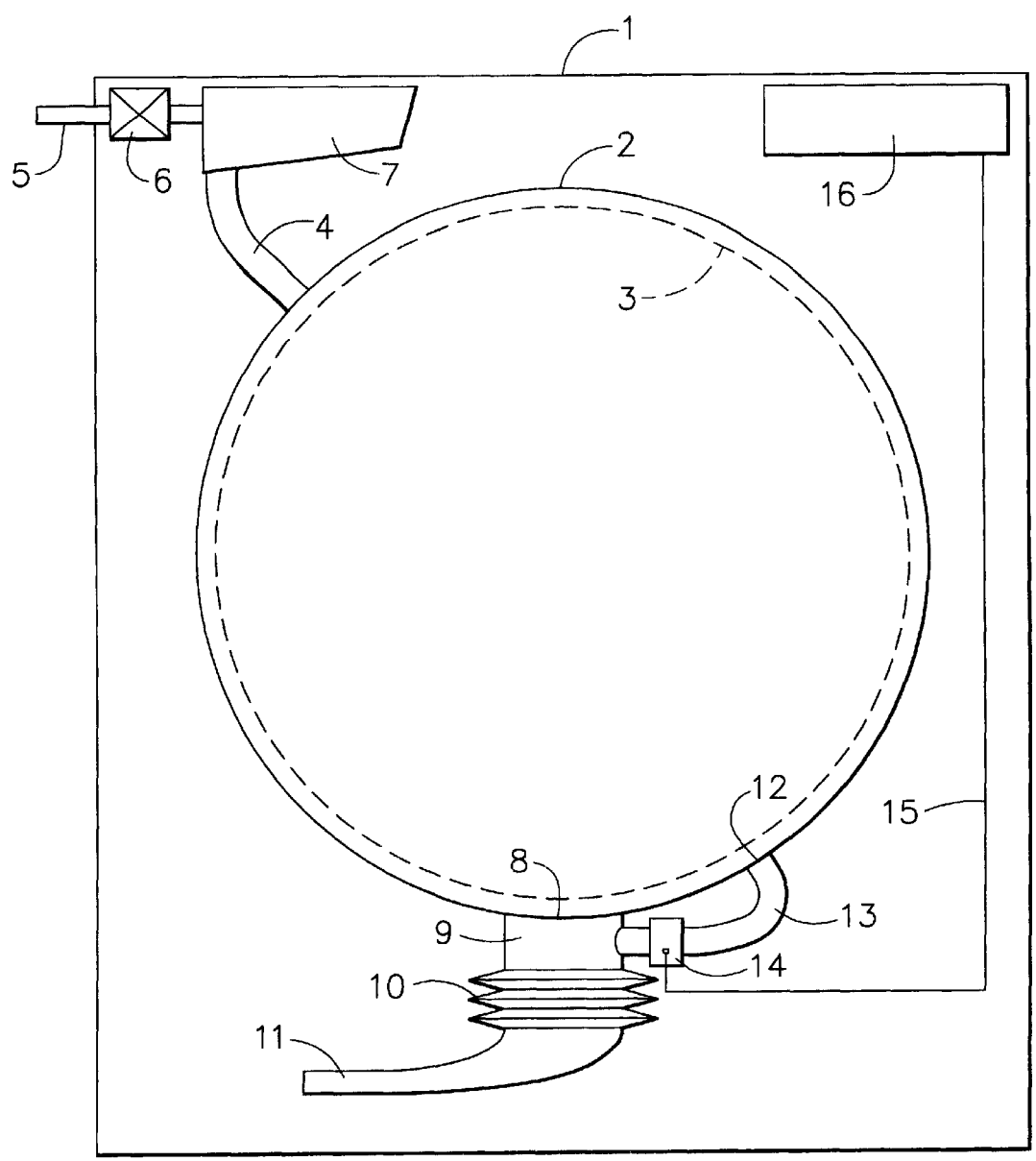
FIG. 1 is a schematic front view of a drum-type washing machine in which embodiments of the present invention may be implemented.

FIG. 1 is a schematic front view of a drum-type washing machine in which a preferred embodiment of the present invention may be utilized. Those skilled in the art can appreciate that the drum-type washing machine illustrated in FIG. 1 represents one example of an environment in which the present invention described herein may be implemented. The present invention is not limited to washing machines, dishwashers and other such machines and environments, but may implemented in any environment in which a need exists to measure the turbidity of fluids, including fresh water, salt water, viscous fluids, and other fluid environments. The drum-type washing machine illustrated in FIG. 1 is thus presented for illustrative purposes only. It can be appreciated that the invention described herein may also utilized for filtration, chemical processing, refining and other liquid-based processes, wherein the drum-type system illustrated in FIG. 1 may be illustrative of a reservoir for various liquids.

The washing machine shown in FIG. 1 has a housing 1, in which a tub 2 (suds container) is mounted. While the specific details of the tub mounting are not illustrated, it is noted that the tub 2 is capable of vibrating. A laundry drum 3 is rotatably supported about a horizontal axis in the tub 2. Water and, optionally, detergent can be supplied to it in the upper portion of the tub 2 via a line 4 from a supply line 5 via a magnet valve 6 and a detergent dispenser 7. A drain line 9 communicates in fluid-tight fashion with a drain opening 8 in the lower portion of the tub 2. The drain line 9 communicates via bellows creases 10 and a further line 11, with a non-illustrated washwater pump fixedly mounted in the housing 1. Located between the drain line 9 and a further opening 12, which is disposed at a somewhat higher geodetic level than the drain opening 8, there is a line segment 13. Due to the level difference between the openings 8 and 12, there is a steady flow of washwater through the line segment 13 during washing machine operation. The flow is thereby into and through the opening 12 to the drain line 9 and back via the drain opening 8 into the tub 2. As noted, the flow is based on the slight pressure differences in the washwater above the drain opening 8 and the opening 12. A sensor 14 may be mounted on the line segment 13, and its output signals are output via a line 15 to a processing and control unit 16. The unit 16 processes the sensor signals. Those skilled in the art can appreciate that there are many other physical locations within housing 1 that can be chosen for the disposition of sensor 14, such as, for example, a pump housing within housing 1.

Figure 2:
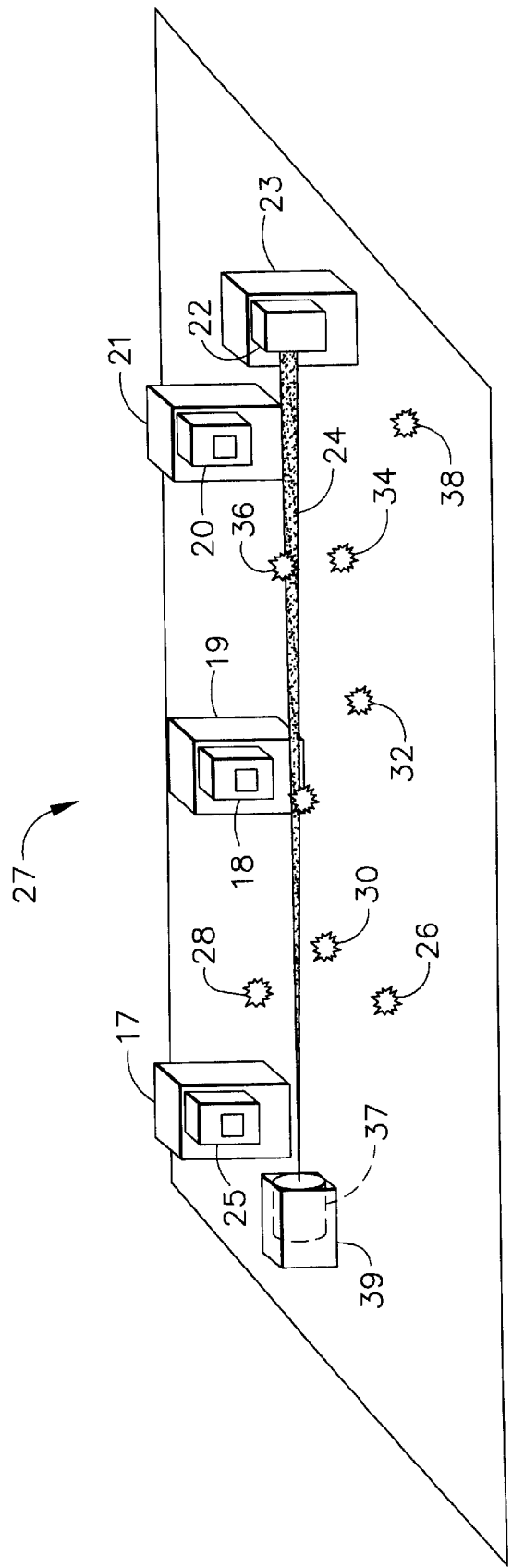
FIG. 2 illustrates a focused laser light turbidity sensor that may be utilized in accordance with preferred embodiments of the present invention.

FIG. 2 illustrates a focused laser light turbidity sensor 27 that may be utilized in accordance with preferred embodiments of the present invention. Laser light turbidity sensor 27 may be configured to operate as a sensor, such as sensor 14 of FIG. 1. Laser light turbidity sensor 27 may also be utilized to measure a variety of turbid environments, including turbid environments composed of liquids and other fluids, such as viscous fluids. Focused laser light turbidity sensor 27 may include a laser light source, such as laser diode 37. Laser diode 37 can be implemented as a low cost laser diode with a focusing lens to create a strong and focused beam of light capable of passing through a wide variety of fluids. Laser diode 37 may be contained within or surrounded by a housing 39.

Thus, laser diode 37 can emit a collimated laser beam 24. Because the beam of this focused laser light is focused, light detectors may be placed close to the incident collimated laser beam 24. The use of a low-cost semiconductor laser diode, such as laser diode 37, thus provides a highly accurate and power light source to create a low-cost turbidity sensor. This light source (i.e., laser diode 37), together with a variety of geometric configurations of light-sensitive detectors, will accurately measure a broad range of particulate concentrations, such as particles 26, 28, 30, 32, 34, 36, and 38 contained within a fluid.

Such light-sensitive detectors may be implemented as semiconductor light detectors and may be configured in a variety of geometric locations with respect to the light source (i.e., laser diode 37). In the configuration illustrated in FIG. 2, a back scatter detector 25 may be located near laser diode 37, while a direct transmission detector 22 is located opposite laser diode 37. A forward scatter detector 20 may be located near direct transmission detector 22. A side scatter detector 18 can be located between back scatter detector 25 and forward scatter detector 20. Back scatter detector 25, side scatter detector 18, forward scatter detector 20, and direct transmission detector 22 may be respectively housed within cavities 17, 19, 21, and 23. Thus, the cell or cavity in which light-sensitive elements of such detectors are housed may be designed to minimize ambient or stray light and eliminate undesirable reflections of incident collimated laser beam 24. Special consideration can be given to the darkening of the cell or cavity to eliminate stray or ambient light and undesirable reflections that may contribute to errors in readings of clean washing fluid in a turbid environment, such as may be encountered in the washing machine depicted in FIG. 1.

Figure 3:
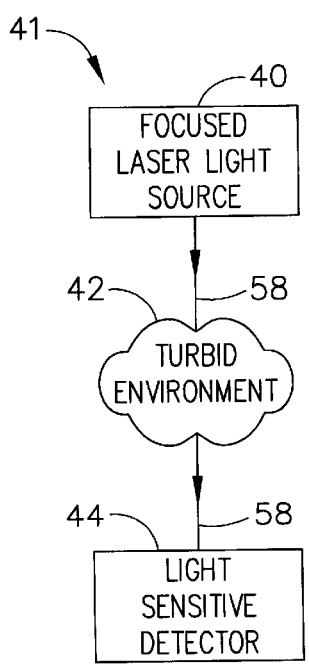
FIG. 3 depicts a high-level block diagram of a focused laser light turbidity sensor, in accordance with preferred embodiments of the present invention.

FIG. 3 depicts a high-level block diagram 41 of a focused laser light turbidity sensor, in accordance with preferred embodiments of the present invention. Note that in the block diagrams in FIGS. 3 to 4 herein similar parts are indicated by identical reference numerals. The focused laser light turbidity sensor illustrated in FIG. 3 includes a focused laser light source 40, which is analogous to laser diode 37 of FIG. 2, and a minimum of one light-sensitive detector 44. Focused laser light source 40 provides a focused light beam 58 with superior intensity that is unique from other light sources.

Light beam 58 can be generated as a focused beam of collimated light that allows for closer placement of light detectors to the incident beam without the use of apertures. Light detectors may be located directly opposite, perpendicular, obtuse, and/or acute to the focused laser light source 40 to gather scattered light from particles in a solution. Light beam 58 passes through a turbid environment 42, which may include a variety of fluids, chemicals, or viscous materials, such as oil. Although only one light sensitive detector 44 is depicted in FIG. 3, it can be appreciated that a plurality of such light sensitive detectors may be utilized in accordance with the focused laser light turbidity sensor illustrated in FIG. 3.

Figure 4:
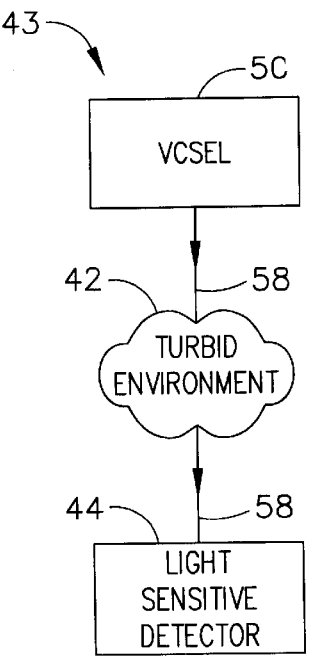
FIG. 4 illustrates a high-level block diagram of a focused laser light turbidity sensor, which utilizes a VCSEL configuration, in accordance with preferred embodiments of the present invention.

FIG. 4 illustrates a high-level block diagram 43 of a focused laser light turbidity sensor, which utilizes a VCSEL (Vertical Cavity Surface Emitting Laser) configuration, in accordance with preferred embodiments of the present invention. Note that in FIGS. 3 and 4 like parts are indicated by like reference numerals. Thus, in place of the focused laser light source illustrated in FIG. 3, a VCSEL 50 may be utilized, as indicated in FIG. 4. VCSELs are well known in the art.

A VCSEL is a type of semiconductor laser, which emits light in a direction that is generally perpendicular to an upper surface of the laser structure. Lasers of this type comprise multiple layers of semiconductive material. Typically, a substrate is provided at one end of a stack of semiconductive layers. On the substrate, a first mirror stack and a second mirror stack may be arranged with a quantum well active region therebetween. On both sides of the active region, graded or ungraded layers can be provided as a spacer between mirrors. On the second mirror stack, an electrical contact may be disposed.

Another electrical contact can be provided at the opposite end of the stack of layers in contact with the substrate. An electrical current is caused to flow between the two contacts. This electrical current, therefore, passes through the second mirror stack, a top graded index region, the first mirror stack and the substrate. Typically, a pre-selected portion of the active layer may be designated as the active region and the electrical current is generally caused to flow through the active region in order to induce lasing.

Those skilled in the art can appreciate that the aforementioned description of a typical VSCEL merely represents one type of VCSEL that may be utilized in accordance with preferred embodiments of the present invention. It can be appreciated that a variety of VCSELs may be utilized in accordance with the present invention. The aforementioned general description of a VCSEL is thus presented herein for illustrative purposes only and should not be interpreted as limiting the type of VCSEL utilized in accordance with the invention described herein.

Figure 5:
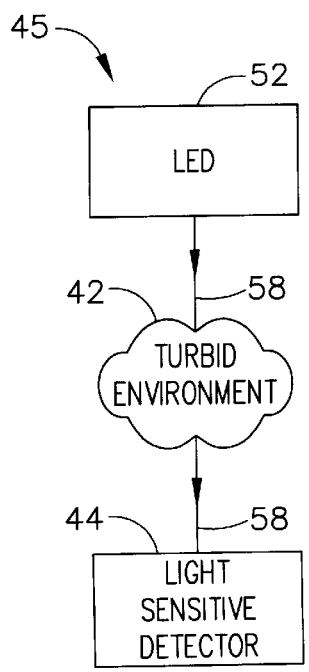
FIG. 5 depicts a high-level block diagram of a focused laser light turbidity sensor, which utilizes an LED configuration, in accordance with preferred embodiments of the present invention.

FIG. 5 depicts a high-level block diagram 45 of a focused laser light turbidity sensor, which utilizes a Light Emitting Diode (LED) configuration, in accordance with preferred embodiments of the present invention. LEDs are well known in the art and are generally configured as a p-n junction diode that emits light as a result of direct radiative recombination of excess electron-hole pairs known. LEDs are generally utilized for low-voltage display devices, such as electrical watches, but may be implemented as a light source in place of focused laser light source 40 of FIG. 3. Those skilled in the art can appreciate that LED 52, as illustrated in FIG. 5, may be implemented as an LED modified to emit a focused or collimated laser light beam. Current LEDs do not emit such collimated laser light, but it is anticipated that LEDs may be developed in the future to emit focused or collimated laser light. LED 52 thus may be utilized in place of focused laser light source 40 of FIG. 3.

Figure 6:
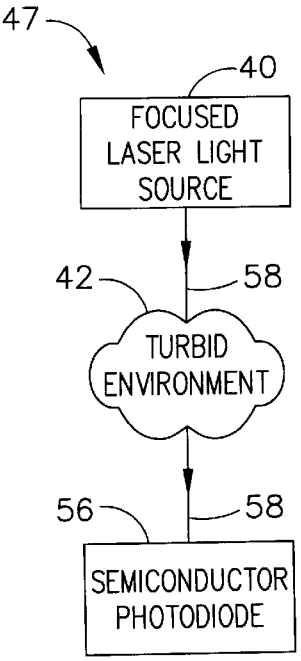
FIG. 6 illustrates a high-level block diagram of a focused laser light turbidity sensor, which utilizes a semiconductor photodiode as a light-sensitive detector, in accordance with preferred embodiments of the present invention.

FIG. 6 illustrates a high-level block diagram 47 of a focused laser light turbidity sensor, which utilizes a semiconductor photodiode as a light-sensitive detector, in accordance with preferred embodiments of the present invention. In the configuration illustrated in FIG. 6, a semiconductor diode may be utilized as a light sensitive detector, such as, for example, light sensitive detector 44 of FIG. 5. Suitable light sensitive elements that may be incorporated into focused light source 40 can include photodiodes and phototransistors.

Figure 7:
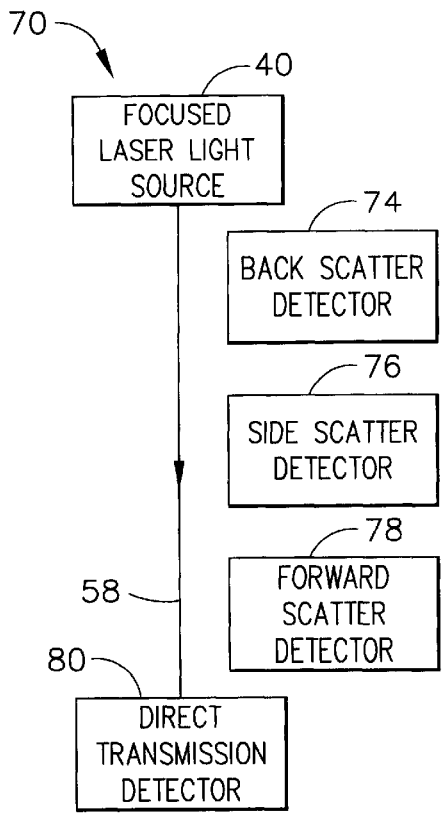
FIG. 7 depicts a high-level block diagram of a focused laser light turbidity sensor, including a back scatter detector, side scatter detector, forward scatter detector, and direct transmission detector, in accordance with preferred embodiments of the present invention.

FIG. 7 depicts a high-level block diagram 70 of a focused laser light turbidity sensor, including a back scatter detector 74, a side scatter detector 76, a forward scatter detector 78, and a direct transmission detector 80, in accordance with preferred embodiments of the present invention. A focused laser light source 40 may emit a focused beam of light (i.e., light beam 58). Back scatter detector 74 of FIG. 7 is generally analogous to back scatter detector 25 of FIG. 2. Similarly side scatter detector 76, forward scatter detector 78, and direct transmission detector 80 of FIG. 7 are respectively analogous to side scatter detector 18, forward scatter detector 20, and direct transmission detector 22 of FIG. 2.

Figure 8:
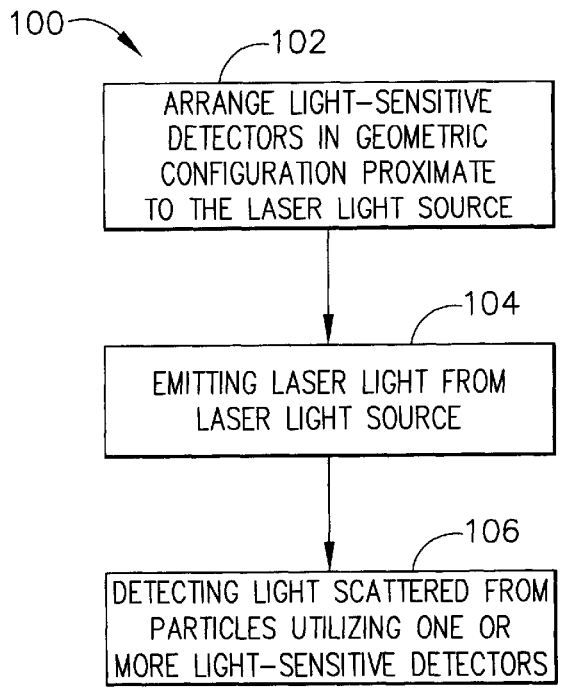
FIG. 8 illustrates a high-level flow chart of operations illustrative of a method for detecting light scattered from particles contained within particulate content in a turbid environment, in accordance with preferred embodiments of the present invention.

FIG. 8 illustrates a high-level flow chart 100 of operations illustrative of a method for detecting light scattered from particles contained within particulate content in a turbid environment, in accordance with preferred embodiments of the present invention. FIG. 8 depicts a general method for measuring a full range of particulate content in a turbid environment. As indicated at block 102, a plurality of light-sensitive detectors may be arranged in a geometric configuration of light-sensitive detectors with respect to the laser light source for the detection of light scattered from particles of the particulate content that come into contact with light emitted from the laser light source. It can be appreciated, however, that only one light-sensitive detector may be required for detecting light scattered from the particles contained with the particulate content. As indicated next at block 104, laser light may be emitted from the laser light source through the particulate content. Thereafter, as illustrated at block 106, light scattered from particles of the particulate content that come into contact with laser light emitted from the laser light source may be detected utilizing at least one light-sensitive detector located proximate to the laser light source, thereby permitting the accurate measurement of the turbidity of the turbid environment.

Figure 9:
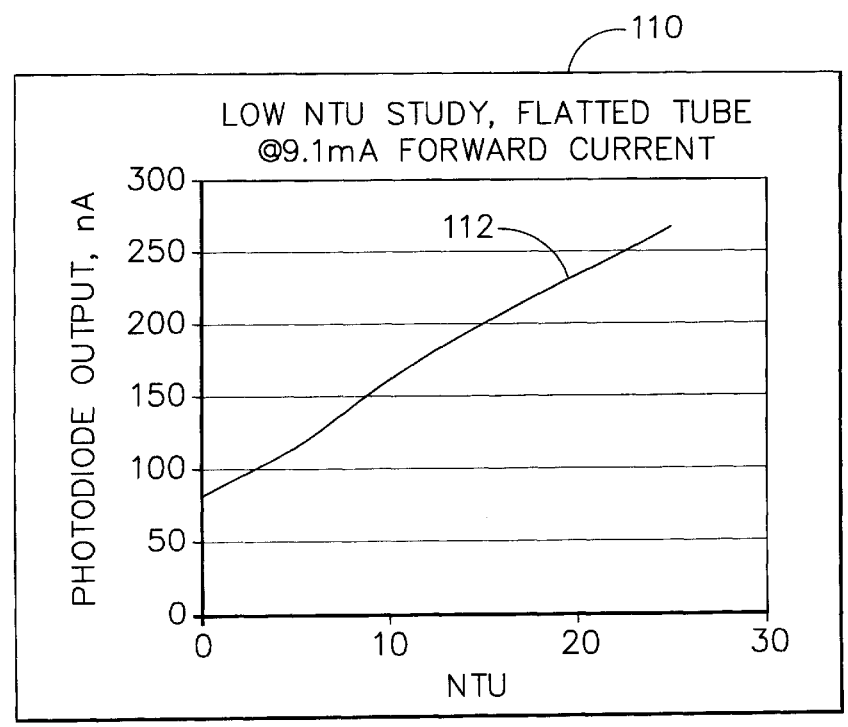
FIG. 9 depicts a plot of low turbidity detected utilizing a turbidity sensor in accordance with the present invention.

FIG. 9 depicts a plot 110 of low turbidity detected utilizing a turbidity sensor in accordance with the present invention. A VCSEL light source may be utilized to obtain the results indicated in plot 110 of FIG. 9. The following results are illustrated in plot 110. In plot 110 nanoamps are measured in a range of 0 to 300 nanoamps along a y-axis, while NTU values of 0 to 30 are measured along the x-axis. Graphical line 112 is based on the following results:

| NTU Level | Nanoamps |
|---|---|
| 0 | 84 |
| 5 | 118 |
| 10 | 166 |
| 15 | 203 |
| 25 | 270 |

Figure 10:
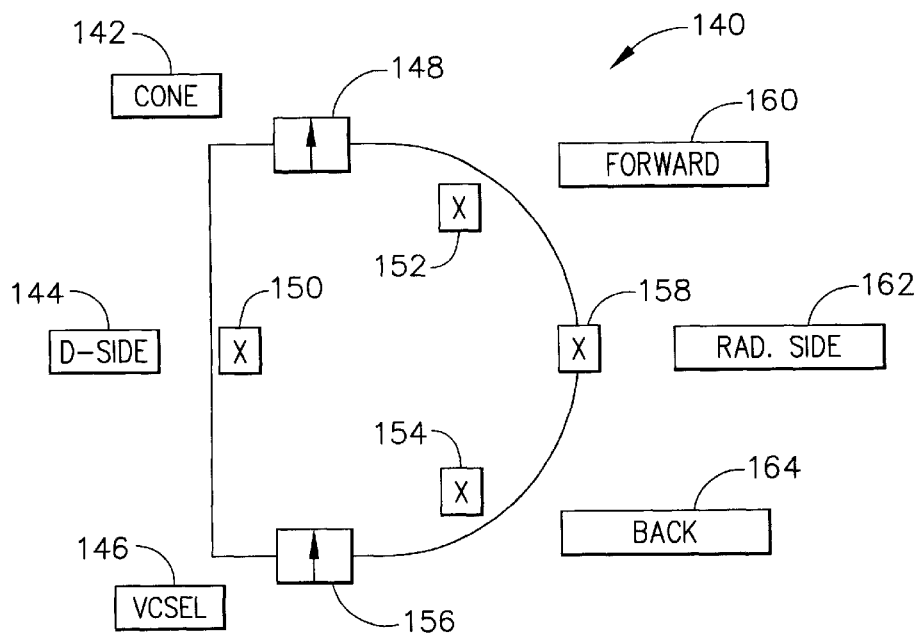
FIG. 10 illustrates a turbidity sensor based on a configuration that includes a D-cell fixture loaded with one photodiode in each position of a geometric arrangement, in accordance with preferred embodiments of the present invention.

FIG. 10 illustrates a turbidity sensor based on a configuration 140 that includes a D-cell fixture loaded with one photodiode in each position of a geometric arrangement, in accordance with preferred embodiments of the present invention. The turbidity sensor arrangement illustrated in FIG. 10 includes a VCSEL 146 located proximate to a d-side detector 144. A cone 142 is located opposite the VCSEL. The d-side detector 144 may be located between VCSEL 146 and cone 142. VCSEL 146 may be configured as a VCSEL light source with 8 mA of forward current. Cone 142 may be implemented as a diffusing cone located opposite the VCSEL light source (i.e., VCSEL 146). A back scatter detector 164 is located opposite a forward scatter detector 160. A side scatter detector 162 may be located on a radial side opposite d-side detector 144. D-side detector 144 may be located at position 150, while the back scatter detector 164 may be located at position 154. A radial side detector 162 can be located at position 158, while forward scatter detector 160 may be located at position 152. Arrows 156 and 148 indicate the general direction light from VCSEL 146 may be emitted.

Figure 11:
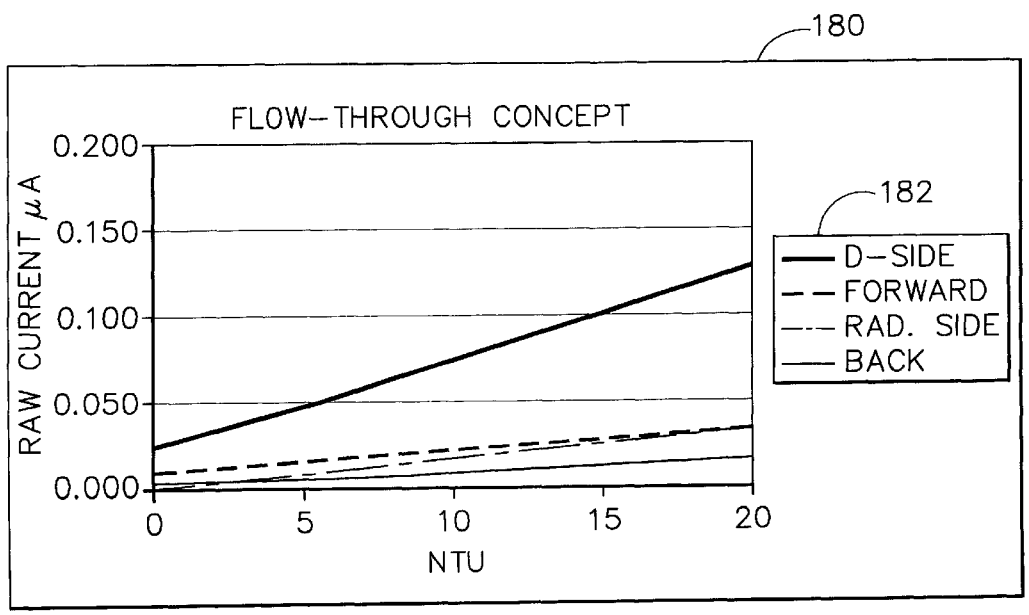
FIG. 11 depicts a plot of turbidity results obtained from the configuration illustrated in FIG. 10, in accordance with preferred embodiments of the present invention.

FIG. 11 depicts a plot 180 of turbidity results obtained from the configuration illustrated in FIG. 10, in accordance with preferred embodiments of the present invention. Index 182 indicates associated graph lines as d-side, forward, radial, or back, which indicate the position of light-sensitive detectors, as illustrated in the configuration of FIG. 10. The results indicated in plot 180 are based on the following collected data:

| NTU Level | d-side | forward | rad. Side | back |
|---|---|---|---|---|
| 0 | 0.001 | 0.025 | 0.004 | 0.010 |
| 5 | 0.009 | 0.049 | 0.006 | 0.015 |
| 20 | 0.034 | 0.130 | 0.016 | 0.035 |

Figure 12:
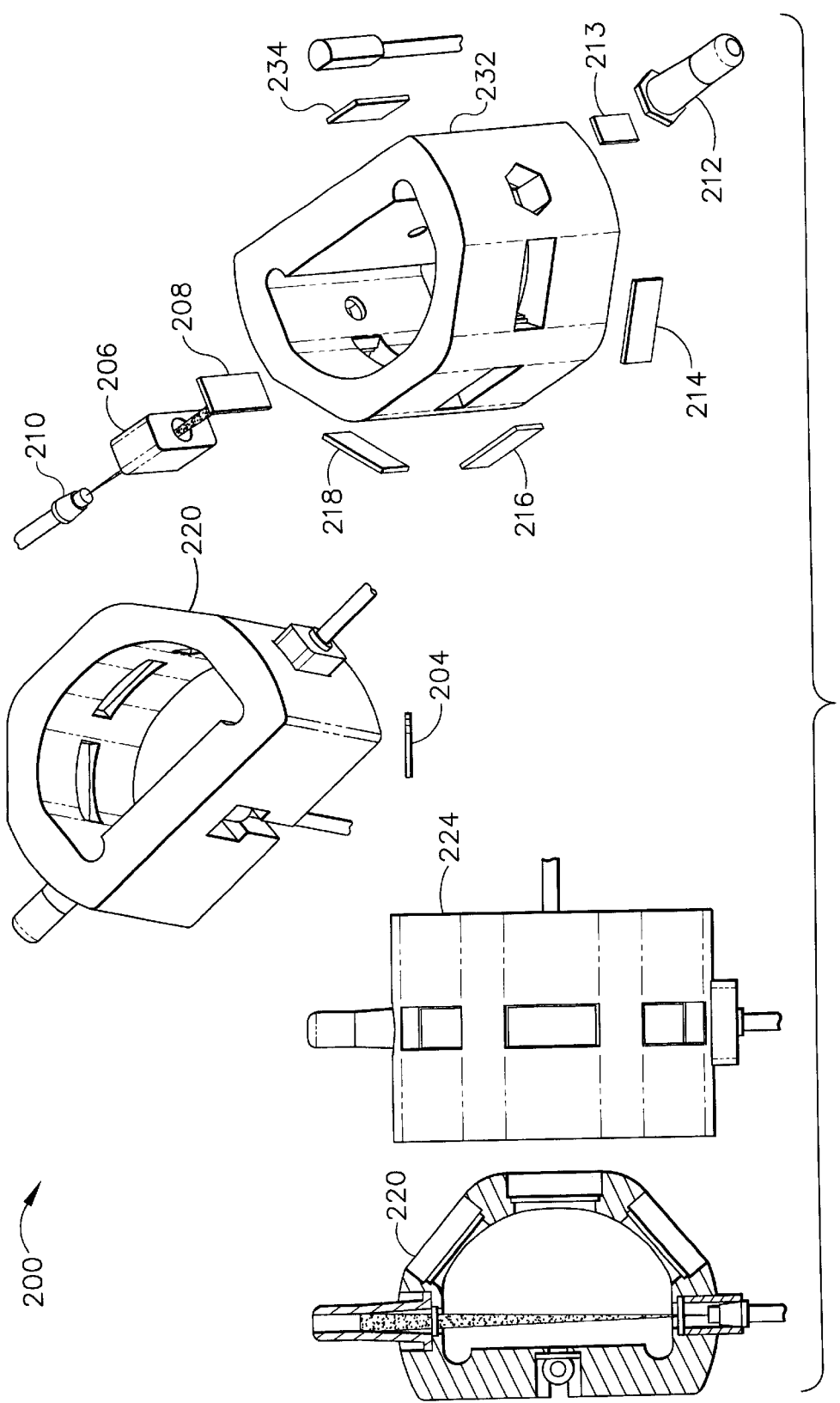
FIG. 12 illustrates sectional views of a turbidity sensor housing that may be utilized in accordance with preferred embodiments of the present invention.

FIG. 12 illustrates sectional views of a turbidity sensor housing 200 that may be utilized in accordance with preferred embodiments of the present invention. Those skilled in the art can appreciate that the sectional views depicted in FIG. 12 represent merely one type of turbidity sensor configuration that may be implemented in accordance with the present invention. Other implementations may also be utilized depending on the requirements of the machine or turbid environment in which the present invention is implemented. A top view 220 of turbidity sensor housing 200 is indicated in FIG. 12, along with a side view 224 of turbidity sensor housing 200. A perspective bottom view 202 of turbidity sensor housing 200 is also indicated with respect to a perspective bottom side view 232 of turbidity sensor housing 200.

Perspective side view 232 can be explained in reference to the configuration illustrated in FIG. 2. Thus, element 216 of FIG. 12 is generally analogous to side scatter detector 18 of FIG. 2, while element 218 is generally analogous to back scatter detector 25 of FIG. 2. Element 214 of FIG. 12 is generally analogous to forward scatter detector 20 of FIG. 2, and element 213, together with element 212, may be generally analogous to direct transmission detector 22 of FIG. 2, including housing 23 in which direct transmission detector 22 is housed. Element 210 of FIG. 12 may be generally analogous to laser diode 37 of FIG. 2. Element 206 of FIG. 12 may be generally analogous to housing 39 of FIG. 2. Element 208 can be implemented as an additional photosensitive element, wherein element 208, housing 206, and laser diode 210 together may compose a VCSEL, which may be generally analogous to VCSEL 146 of FIG. 10. The turbidity sensor configuration illustrated in FIG. 12 may be generally shaped like the letter "D". Thus, when referring to the turbidity sensor configurations illustrated in FIG. 12 and FIG. 10, such configurations may be referred to as a "D-cell fixture". An element 234, along with elements 218, 216, 214, 213, and 208 of FIG. 12 may be implemented as a photodiode or other photosensitive element. Element 204 may also be configured as a photodiode or other photosensitive element.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

The embodiments of an invention in which an exclusive property or right is claimed are defined as follows:

1. A turbidity sensor for measuring a full range of particulate content in a turbid environment, said turbidity sensor comprising:
   a laser light source for emitting laser light through said particulate content; and
   a back scatter light-sensitive detector located proximate to said laser light source for the detection of light scattered back from particles of said particulate content that come into contact with laser light emitted from said laser light source, thereby permitting the accurate measurement of the turbidity of said turbid environment, wherein said light-sensitive detector is located acute to said laser light source.

2. The turbidity sensor of claim 1 additionally comprising:
   a side scatter detector.

3. The turbidity sensor of claim 1 additionally comprising:
   a forward scatter detector.

4. The turbidity sensor of claim 1 additionally comprising:
   a direct transmission detector.

5. The turbidity sensor of claim 1 additionally comprising:
   a plurality of further light-sensitive detectors, wherein said back scatter light-sensitive detector and said further light-sensitive detectors are arranged in a geometric configuration of light-sensitive detectors with respect to said laser light source.

6. The turbidity sensor of claim 1 additionally comprising:
a light-sensitive detector located directly opposite said laser light source to gather light transmitted through said particulate content.

7. The turbidity sensor of claim 1 additionally comprising:
a light-sensitive detector located perpendicular to said laser light source to gather light scattered from said particulate content.

8. The turbidity sensor of claim 1 additionally comprising:
a light-sensitive detector located obtuse to said laser light source to gather light scattered from said particulate content.

9. The turbudity sensor of claim 1 wherein said light-sensitive detector comprises a semiconductor photodiode.

10. The turbidity sensor of claim 1 wherein said light-sensitive detector includes a housing in which light-sensitive elements are maintained, and wherein said housing is configured to minimize ambient light and eliminate undesirable reflections from said laser light transmitted from said laser light source.

11. The turbidity sensor of claim 1 wherein said laser light source comprises a laser diode.

12. The turbidity sensor of claim 11 wherein said laser light source emits a focused beam of light capable of passing through said particulate content in said turbid environment.

13. The turbidity sensor of claim 1 wherein said laser light transmitted from said laser light source comprises a collimated beam of laser light.

14. The turbidity sensor of claim 1 wherein said laser light source comprises a Vertical Cavity Surface Emitting Laser (VCSEL).

15. The turbidity sensor of claim 1 wherein said turbid environment comprises a fluid environment.

16. The turbidity sensor of claim 1 wherein said turbid environment comprises a viscous environment.

17. A method for measuring a full range of particulate content in a turbid environment, said method comprising:
emitting laser light from a laser light source through said particulate content; and
detecting light scattered from particles of said particulate content that come into contact with laser light emitted from said laser light source utilizing a light-sensitive detector located proximate to said laser light source and at a non-perpendicular angle with respect to the emitted laser light, thereby permitting the accurate measurement of the turbidity of said turbid environment.

18. The method of claim 17 wherein said light-sensitive detector comprises:
a back scatter detector.

19. The method of claim 17 additionally comprising:
a side scatter detector.

20. The method of claim 17 wherein said light-sensitive detector comprises:
a forward scatter detector.

21. The method of claim 17 additionally comprising:
a direct transmission detector.

22. The method of claim 17 further comprising:
arranging said light-sensitive detector in addition to other light-sensitive detectors in a geometric configuration of light-sensitive detectors with respect to said laser light source for the detection of light scattered from particles of said particulate content that come into contact with light emitted from said laser light source.

23. The method of claim 17 further comprising:
locating an additional light-sensitive detector directly opposite said laser light source to gather light transmitted through said particulate content.

24. The method of claim 17 further comprising:
locating an additional light-sensitive detector perpendicular to said laser light source to gather light scattered from said particulate content.

25. The method of claim 17 further comprising:
locating the light-sensitive detector obtuse to said laser light source to gather light scattered from said particulate content.

26. The method of claim 17 further comprising:
locating the light-sensitive detector acute to said laser light source to gather light scattered from said particulate content.

27. The method of claim 17 wherein said light-sensitive detector comprises a semiconductor photodiode.

28. The method of claim 17 further comprising:
locating said light-sensitive detector within a housing in which light-sensitive elements are maintained; and
configuring said housing to minimize ambient light and eliminate undesirable reflections from said laser light transmitted from said laser light source.

29. The method of claim 17 wherein said laser light source comprises a laser diode.

30. The method of claim 29 further comprising:
emitting said laser light source from said laser light source as a focused beam of light capable of passing through said particulate content in said turbid environment.

31. The method of claim 29 further comprising:
emitting said laser light source from said laser light source as a collimated beam of laser light.

32. The method of claim 17 wherein said laser light source comprises a Vertical Cavity Surface Emitting Laser (VCSEL).

33. The method of claim 17 wherein said turbid environment comprises a fluid environment.

34. The method of claim 17 wherein said turbid environment comprises a viscous environment.

35. A turbidity sensor for measuring a full range of particulate content in a turbid environment, said turbidity sensor comprising:
a laser light source for emitting laser light through said particulate content; and
a forward scatter light-sensitive detector located proximate to said laser light source for the detection of light scattered forward from particles of said particulate content that come into contact with laser light emitted from said laser light source, thereby permitting the accurate measurement of the turbidity of said turbid environment, wherein said light-sensitive detector is located obtuse to said laser light source.

36. The turbidity sensor of claim 35 additionally comprising:
a back scatter detector.

37. The turbidity sensor of claim 35 additionally comprising:
a side scatter detector.

38. The turbidity sensor of claim 35 additionally comprising:
a direct transmission detector.

39. The turbidity sensor of claim 35 additionally comprising:
a plurality of further light-sensitive detectors, wherein said back scatter light-sensitive detector and said further light-sensitive detectors are arranged in a geometric configuration of light-sensitive detectors with respect to said laser light source.

40. The turbidity sensor of claim 35 additionally comprising:
   a light-sensitive detector located directly opposite said laser light source to gather light transmitted through said particulate content.

41. The turbidity sensor of claim 35 additionally comprising:
   a light-sensitive detector located perpendicular to said laser light source to gather light scattered from said particulate content.

42. The turbidity sensor of claim 39 additionally comprising:
   a light-sensitive detector located acute to said laser light source to gather light scattered from said particulate content.

43. The turbidity sensor of claim 35 wherein said light-sensitive detector comprises a semiconductor photodiode.

44. The turbidity sensor of claim 35 wherein said light-sensitive detector includes a housing in which light-sensitive elements are maintained, and wherein said housing is configured to minimize ambient light and eliminate undesirable reflections from said laser light transmitted from said laser light source.

45. The turbidity sensor of claim 35 wherein said laser light source comprises a laser diode.

46. The turbidity sensor of claim 39 wherein said laser light source emits a focused beam of light capable of passing through said particulate content in said turbid environment.

47. The turbidity sensor of claim 35 wherein said laser light transmitted from said laser light source comprises a collimated beam of laser light.

48. The turbidity sensor of claim 35 wherein said laser light source comprises a Vertical Cavity Surface Emitting Laser (VCSEL).

49. The turbidity sensor of claim 35 wherein said turbid environment comprises a fluid environment.

50. The turbidity sensor of claim 35 wherein said turbid environment comprises a viscous environment.

* * * * *